United States Patent
Zeng et al.

(10) Patent No.: US 11,098,168 B2
(45) Date of Patent: Aug. 24, 2021

(54) METHOD FOR PREPARING CROSS-LINKED HYALURONIC ACID GEL AND CROSS-LINKED HYALURONIC ACID GEL PREPARED BY THE SAME

(71) Applicant: Hangzhou Singclean Medical Products Co., Ltd., Zhejiang (CN)

(72) Inventors: Jin Zeng, Zhejiang (CN); Weiwei Wang, Zhejiang (CN); Weiqing Sun, Zhejiang (CN)

(73) Assignee: Hangzhou Singclean Medical Products Co., Ltd., Hangzhou (CN)

( * ) Notice: Subject to any disclaimer, the term of this patent is extended or adjusted under 35 U.S.C. 154(b) by 147 days.

(21) Appl. No.: 16/454,089

(22) Filed: Jun. 27, 2019

(65) Prior Publication Data

US 2020/0095383 A1 Mar. 26, 2020

(30) Foreign Application Priority Data

Sep. 21, 2018 (CN) .......................... 201811106059.3

(51) Int. Cl.
| | |
|---|---|
| *C08J 3/075* | (2006.01) |
| *A61K 9/06* | (2006.01) |
| *A61K 47/36* | (2006.01) |
| *A61L 27/20* | (2006.01) |
| *A61L 27/52* | (2006.01) |
| *A61L 27/60* | (2006.01) |

(52) U.S. Cl.
CPC ................. *C08J 3/075* (2013.01); *A61K 9/06* (2013.01); *A61K 47/36* (2013.01); *A61L 27/20* (2013.01); *A61L 27/52* (2013.01); *A61L 27/60* (2013.01); *A61L 2430/06* (2013.01); *C08J 2305/08* (2013.01)

(58) Field of Classification Search
None
See application file for complete search history.

(56) References Cited

FOREIGN PATENT DOCUMENTS

| | | | | |
|---|---|---|---|---|
| CN | 101367884 A | | 2/2009 | |
| CN | 104491854 A | * | 4/2015 | ........... A61K 39/102 |
| CN | 104892962 A | | 9/2015 | |
| CN | 105969825 A | | 9/2016 | |
| CN | 106397846 A | * | 2/2017 | ............. A61K 47/36 |
| WO | WO-2017005362 A1 | * | 1/2017 | ......... A61F 9/00781 |

OTHER PUBLICATIONS

Cui, N., Qian, J., Xu, W., Xu, M., Zhao, N., Liu, T., & Wang, H. (2016). Preparation, characterization, and biocompatibility evaluation of poly (Nε-acryloyl-l-lysine)/hyaluronic acid interpenetrating network hydrogels. Carbohydrate polymers, 136, 1017-1026. (Year: 2016).*

* cited by examiner

*Primary Examiner* — Dale R Miller

(57) ABSTRACT

Related to is the field of polymer materials, and particularly related to are a method for preparing cross-linked hyaluronic acid gel and a cross-linked hyaluronic acid gel prepared by the method. Under an alkaline condition, a disulfide cross-linking agent is dropwise added into an alkaline solution of hyaluronic acid for cross-linking reaction, and after the reaction is completed, dialysis and freeze drying are carried out to obtain the cross-linked hyaluronic acid gel. A new disulfide cross-linking agent N,N-bis(acroloyl)cystamine is introduced, and it effectively solves degradation regulating problems of cross-linked hyaluronic acid; the disulfide bond ratio is controllable, which can effectively improve a cross-linking modification degree ratio in the cross-linked hyaluronic acid, thereby solving the problem of difficult degradation of highly cross-linked hyaluronic acid gel in the past. The cross-linked material has potential applications in aspects of drug carriers and tissue engineering scaffolds.

15 Claims, No Drawings

METHOD FOR PREPARING CROSS-LINKED HYALURONIC ACID GEL AND CROSS-LINKED HYALURONIC ACID GEL PREPARED BY THE SAME

CROSS REFERENCE TO RELATED APPLICATIONS

The present application claims the benefit of Chinese Patent Application No. 201811106059.3 filed on Sep. 21, 2018, the contents of which are incorporated herein by reference in their entirety.

FIELD OF THE INVENTION

The present disclosure belongs to the technical field of polymer materials, and in particular relates to a method for preparing thiolated hyaluronic acid and cross-linked hyaluronic acid gel prepared by the same.

BACKGROUND OF THE INVENTION

Hyaluronic acid (HA), also referred to as hyaluronan, is one of the most representative mucopolysaccharides, and is widely present in various parts of a human body. Due to its unique molecular structure and physicochemical properties, hyaluronic acid shows multiple important physiological functions in an organism, for example, lubricating joints, regulating the permeability of blood vessel walls, regulating proteins, regulating the diffusion and transportation of water-electrolytes and promoting wound healing. In addition, hyaluronic acid has a specific water-locking function, and as the best moisturizing substance found at present in nature, hyaluronic acid is considered as an ideal natural moisturizing factor.

Hyaluronic acid is a polymer mucopolysaccharide with D-N-acetylglucosamine and D-glucuronic acid as structural units, and is a transparent natural polysaccharide colloidal crystal. The polysaccharide chain of hyaluronic acid contains three functional group types which can be derived, namely, hydroxyl, carboxyl and acetamido. Due to the extremely high molecular weight of the polymer, these residual terminal groups are generally not considered, and many HA derivatives can be obtained by reacting different chemical reagents with these functional groups, whereas the actual significance of various HA derivatives depends on application of the HA derivatives in the field of medicine.

HA and derivatives thereof can provide unique biocompatibility, rheological property, and chemical and physical diversity in aspects of postoperative anti-adhesion, drug sustained release, ophthalmological field, arthritis treatment, percutaneous embolotherapy, soft tissue repair and enlargement. Modified HA can be applied in terms of many physical properties (such as fluid, gel and solid), and its rheological property and in-vivo retention time are increased, which expands their applications. The biocompatibility inhered in HA and derivatives thereof and their unique physical properties ensure their continuous applications.

The specification of patent application CN101367884A discloses the obtaining of thiolated hyaluronic acid by using hyaluronic acid as a raw material with an addition of a compound containing a disulfide bond, and then reducing the disulfide bond with dithiothreitol and the like to form sulfydyl. This is achieved mainly by reacting the carboxyl of hyaluronic acid with the amido of the disulfide compound; the pH value of the reaction system needs to be regulated for several times; and the reaction time is relatively long. The specification of patent application CN105969825A discloses that sulfydryl hyaluronic acid is used as a raw material, horseradish peroxidase is used as a raw material, and cross linking is carried out through a reverse emulsion method in combination with horseradish peroxidase to form a gel containing a disulfide bond; an oil-to-water ratio is then regulated, and a non-ionic surface active agent is added and mixed in an oil phase; and the reaction is complex to operate. CN104892962A discloses a preparation method of a sulfydryl/disulfide bond-controllable self-cross-linked hyaluronic acid gel, in which hyaluronic acid reacts with cysteamine dihydrochloride first to obtain sulfydryl hyaluronic acid, and then oxidation is carried out between sulfydryl groups to form a disulfide bond; the gel is formed in an incubator at 37° C. in the reaction process, and the reaction process is complex.

At present, most of the hyaluronic acid products on the market use divinyl sulphone, 1,4-butanediol diglycidyl ether, glycerinum diglycidyl ether, ethylene glycol diglycidyl ether and other substances as cross-linking agents to improve mechanical property thereof. However, research on the degradation property of hyaluronic acid is generally only performed through hyaluronidase, but hyaluronidase is expensive. There have been few reports about the preparation of cross-linked hyaluronic acid gel with a disulfide cross-linking agent. Disulfide cross-linking agents that have been reported are 2,2-dithiodiamide, 3,3-dithiodiacrylamide, and 2,2-dithiodiacethydrazide. When these cross-linking agents are used for hyaluronic acid reaction, the carboxyl of hyaluronic acid has to be first activated; the reaction time is relatively long, and the pH value of the reaction system has to be regulated 3-4 times; and the whole process is tedious and complex.

SUMMARY OF THE INVENTION

Due to its unique molecular structure and physicochemical properties, hyaluronic acid exhibits multiple important functions in an organism, and is widely applied clinically. Hyaluronic acid has a good biocompatibility and biodegradability, but hyaluronic acid that is not cross-linked remains only a short time in vivo and degrades very rapidly, which limits its application prospects in many aspects. In order to prolong the in-vivo retention time of hyaluronic acid, a modification or cross-linking method is usually used to improve the mechanical strength and to reduce the degradation rate of hyaluronic acid. At present, commonly used cross-linking agents, such as divinylsulfone and 1,4-butanedioldiglycidyl ether, can only regulate the degradation time of hyaluronic acid by cross-linking degree, which is rather difficult to achieve clinically, especially when hyaluronic acid is used as a degradation-controllable tissue engineering material.

In order to overcome the uncontrollability problem of cross-linked hyaluronic acid in the existing technologies, the present disclosure aims to provide a new method for preparing cross-linked hyaluronic acid. The method is simple in process, and the cross-linked network of the prepared cross-linked hyaluronic acid contains a disulfide bond that is easy to break under a reducing condition. The present disclosure adopts the following technical solutions.

Provided is a method for preparing a cross-linked hyaluronic acid gel, including carrying out a cross-linking reaction in an alkaline aqueous solution of hyaluronic acid. In an embodiment, a cross-linking agent used in the cross-linking reaction is N,N-bis(acroloyl)cystamine.

In a preferred embodiment of the present application, the alkaline aqueous solution of hyaluronic acid is prepared by dissolving hyaluronic acid into a 1% alkaline aqueous solution, the alkali including one or two of sodium hydroxide and potassium hydroxide.

In a preferred embodiment of the present application, a mass ratio of hyaluronic acid to the cross-linking agent is (1-30):1, preferably, (3-10):1.

The method of the present disclosure is a free-radical reaction whose cross-linking time is shorter than that of other chemical reactions, and the reaction time is from 10 to 18 hours.

In a preferred embodiment of the present application, the reaction is carried out at a temperature ranging from 40 to 50° C.

In a preferred embodiment of the present application, after the cross-linking reaction is completed, dialysis and freeze drying are carried out so as to obtain a cross-linked hyaluronic acid gel.

In a preferred embodiment of the present application, a phosphate buffer for the dialysis has a concentration of phosphate preferably ranging from 0.1 to 0.2 M, and a pH value ranging from 7.0 to 7.4. The dialysis is conducted for 36 to 68 hours, preferably, for 48 to 54 hours.

In a preferred embodiment of the present application, the freeze drying includes a a first-stage pre-freezing at a temperature ranging from −65 to −45° C. for 2 to 6 hours, a second-stage sublimation being carried out at a temperature ranging from −30 to −25° C. for 4 to 8 hours and then at a temperature ranging from −10 to 0° C. for 3 to 8 hours, and a third-stage desorption drying at a temperature ranging from 5 to 25° C. for 3 to 8 hours.

In the cross-linked hyaluronic acid gel material prepared by using the method of the present disclosure, the three-dimensional network of the obtained gel contains disulfide bonds distributed therein. When the gel material is endowed with redox properties, it can be controllably degraded in the presence of a reductive small molecule such as dithiothreitol (DTT) or glutathione (GHS). Further, a concentration of the reductive small molecule ranges from 1 to 10 mM.

The cross-linked hyaluronic acid gel prepared by the method of the present disclosure can be used for loading and controllable release of anticancer drugs. After arriving at a lesion region, the scaffold material starts degrade in the presence of in-vivo GSH, thereby achieving targeted release of drugs and improving a healing rate.

The cross-linked hyaluronic acid gel prepared by the method of the present disclosure can be used as tissue engineering scaffold materials, meets requirements of adjustable degradation rate of a cell scaffold material, non-toxic degradation products, and good affinity between a material and a tissue, and is suitable for use as a scaffold material for supporting growth of seed cells in skin repair and cartilage repair.

Compared with the existing technologies, the present disclosure has the following beneficial effects.

In the method for preparing a cross-linked hyaluronic acid gel provided by the present disclosure, a small molecule containing a disulfide bond may used as a cross-linking agent to perform a cross-linking reaction with hyaluronic acid. This method has advantages in its easily available raw materials, mild reaction conditions, one-step cross-linking reaction, high cross-linking efficiency, simple process and posttreatment, and easy operations. The cross-linked hyaluronic acid obtained through cross-linking reaction has a three-dimensional network structure, a good mechanical property and mechanical performance, and can be used as a good drug carrier and tissue engineering scaffold material.

In the cross-linked hyaluronic acid gel material prepared by the method of the present disclosure, its cross-linked network contains a disulfide bond that is easy to break under a reducing condition, and its degradation rate can be regulated in vitro. Compared with the cross-linked hyaluronic acid gel prepared with other traditional cross-linking agents, which degrades only in the presence of hyaluronidase which is expensive, the cross-linked hyaluronic acid gel obtained by the method of the present disclosure can be controlled to degrade in the presence of a reductive small molecule. In addition, factors such as the cross-linking degree, the concentration of the reductive small molecule, and the reaction time provide multiple choices for regulation of the degradation rate, and the degradation rate of the obtained material is macroscopically controllable.

The cross-linked hyaluronic acid gel containing the disulfide bond that is easy to break under the reducing condition prepared by the method of the present disclosure is prepared by way of a cross linking reaction in the alkaline solution of hyaluronic acid, and can be used for loading and delivering an anti-cancer drug, achieving controlled release of the drug in cancer cells. Hyaluronic acid easily binds to CD44 on the surface of a tumor cell membrane to target tumor tissues and enter tumor cells via endocytosis. In addition, the pH of tumor tissues is acidic relative to normal tissues and can induce the controlled release of an anticancer drug. The concentration of reductive glutathione in tumor tissues and cells is far larger than that in normal cells, and therefore the hyaluronic acid drug carrier cross-linked by the disulfide bond can utilize such concentration difference to achieve controlled release of a tumor targeted drug.

The cross-linked hyaluronic acid gel prepared by using the method of the present disclosure can be used as a cell scaffold for loading seed cells, and can be used for wound repair and cartilage repair.

DETAILED DESCRIPTION OF THE EMBODIMENTS

The present disclosure will be further explained through the following examples, but is not limited thereto.

I Preparation Method of a Cross-Linked Hyaluronic Acid Gel

Example 1

Hyaluronic acid (1.0 g) (molecular weight: 900,000-1,100,000) was dissolved into 100 mL 1% alkaline aqueous solution, followed by a dropwise addition of 0.25 g N,N'-bis(acroloyl)cystamine dissolved in 5 mL acetonitrile. The resultant solution was stirred for a reaction at 45° C. for 12 hours. The solution was subjected to dialysis for 50 hours in a phosphate buffer having a pH value of 7.4, pre-freezed a −50° C. for 4 hours, maintained at −30° C. for 7 hours, maintained at −8° C. for 6 hours, and then subjected to desorption drying at 20° C. for 4 hours, to obtain a cross-linked hyaluronic acid gel.

Example 2

Hyaluronic acid (1.0 g) (molecular weight: 900,000-1,110,000) was dissolved into 80 mL 1% alkaline aqueous solution, followed by a dropwise addition of 0.2 g N,N'-bis (acroloyl)cystamine dissolved in 5 mL acetonitrile. The resultant solution was stirred for a reaction at 45° C. for 12 hours. The solution was subjected to dialysis for 50 hours in a phosphate buffer having a pH value of 7.4, pre-freezed at −50° C. for 4 hours, maintained at −30° C. for 7 hours, maintained at −8° C. for 6 hours, and then subjected to desorption drying at 20° C. for 4 hours, to obtain a cross-linked hyaluronic acid gel.

Example 3

Hyaluronic acid (1.0 g) (molecular weight: 1,700,000-1,900,000) was dissolved into 80 mL 1% alkaline aqueous solution, followed by a dropwise addition of 0.15 g N,N'-bis(acroloyl)cystamine dissolved in 5 mL acetonitrile. The resultant solution was stirred for a reaction at 45° C. for 12 hours. The solution was subjected to dialysis for 50 hours in a phosphate buffer having a pH value of 7.4, pre-freezed at −50° C. for 4 hours, maintained at −30° C. for 7 hours, maintained at −8° C. for 6 hours, and then subjected to desorption drying at 20° C. for 4 hours, to obtain a cross-linked hyaluronic acid gel.

Example 4

Hyaluronic acid (1.0 g) (molecular weight: 1,000,000) was dissolved into 80 mL 1% alkaline aqueous solution, followed by a dropwise addition of 0.1 g N,N'-bis(acroloyl) cystamine dissolved in 5 mL acetonitrile. The resultant solution was stirred for a reaction at 45° C. for 12 hours. The solution was subjected to dialysis for 50 hours in a phosphate buffer having a pH value of 7.4, pre-freezed at −50° C. for 4 hours, maintained at −30° C. for 7 hours, maintained at −8° C. for 6 hours, and then subjected to desorption drying at 20° C. for 4 hours, to obtain a cross-linked hyaluronic acid gel.

II Measurement of Pore Diameter of Cross-Linked Hyaluronic Acid Gel

Method: A gel material subjected to freeze drying was cut into 1×1 cm small blocks, and the thickness of the material was measured with a vernier caliper. A result shows that with the increase of an input amount of a cross-linking agent, hyaluronic acid has gradually decreased and relatively uniform pores. When the proportion of the amount of the cross-linking agent relative to hyaluronic acid is larger than 25%, the obtained gel has pores which are too small, and when used as a cell scaffold material, the gel is not conducive to exchange of nutrient substances when cells are cultured. When the proportion of the amount of the cross-linking agent relative to hyaluronic acid is 10-15%, the obtained material has uniform pores and a suitable pore diameter, and the material can provide a microenvironment for cell growth taking advantage of proliferation and growth of cells, and the obtained gel material is suitable for use as a cell scaffold material.

TABLE 1

Pore Diameters of Cross-Linked Hyaluronic Acid Gel Materials Obtained in Examples 1-4

| Sample No. | Cross-linking agent/hyaluronic Acid (w/w %) | Pore Diameter (μm) |
| --- | --- | --- |
| 1-1 | 25% | 85 ± 13 |
| 1-2 | 20% | 92 ± 16 |
| 1-3 | 15% | 99 ± 14 |
| 1-4 | 10% | 113 ± 19 |

III Measurement of Tension Force of Cross-Linked Hyaluronic Acid Gel

Method: The cross-linked hyaluronic acid gel obtained in Examples 1-4 was cut into 3×3 cm small patches, and tension properties of the obtained materials were measured using a tension machine. A result shows that when the proportion of a disulfide cross-linking agent is relatively high, the obtained scaffold material has a relatively high mechanical strength. The scaffold material fractures at a tension force ranges from 5 to 7 N, which ensures that when the cross-linked hyaluronic acid gel prepared by using the method of the present disclosure is used as a cell scaffold, it does not cause damage and fracture of the material during transfer in a transplantation process, and can support growth of cells and provide a microenvironment for growth of cells. When the cross-linking degree is low, the scaffold material has a nonuniform thickness; the material fractures at a thicker position when the tension force ranges from 2 to 4 N, and fractures at a thinner position when the tension force ranges from 1 to 3 N.

TABLE 2

Tensile Strength of Cross-Linked Hyaluronic Acid Cell Scaffolds Obtained in Examples 1-4

| Sample No. | Cross-linking agent/hyaluronic acid (w/w %) | Tension force (N) |
| --- | --- | --- |
| 1-1 | 25% | 5.8 ± 0.8 |
| 1-2 | 20% | 4.6 ± 1.1 |
| 1-3 | 15% | 4.2 ± 0.6 |
| 1-4 | 10% | 2.7 ± 1.2 |

IV Redox Ability of a Cross-Linked Hyaluronic Acid Gel

Method: A cross-linked hyaluronic acid gel material (1-2) was cut into small fragments; 3 parts of the fragments were weighed with each part being 20 mg each part, and were then respectively added into 10 mM PBS buffer solution of GSH (pH=7.4). The resultant solution was placed in a thermostatic water bath of 37° C., followed by magnetic stirring. After the reaction was carried out for a certain time, the content of free hyaluronic acid after cracking was detected. 2 mL supernate was then taken and diluted for determination of the content of uronic acid.

GSH (glutathione) is considered as an important redox couple in animal cells, and it determines anti-oxidant capacity of cells, especially, when a cell nucleus contains a relatively high concentration of GSH. Therefore, a redox drug carrier material containing the disulfide bond can perform controlled release of drugs in cells, and a product produced by the cracking has no side effects on growth of cells. Free hyaluronic acid obtained by cracking the cross-linked hyaluronic acid gel was detected under the condition that the concentration of GSH is 10 mM. A result is shown in Table 3, and it shows that the cross-linked hyaluronic acid cell scaffold can gradually crack with the passage of time under a reducing condition until it becomes a solution state. In addition, the larger the concentration of a reducing agent is, the faster the three-dimensional structure of the obtained scaffold material cracks. Therefore, this cross-linked hyaluronic acid gel has potential applications in the aspects of drug carriers and tissue engineering cell scaffolds.

TABLE 3

Redox Ability of Cross-Linked Hyaluronic Acid Cell Gels Obtained in Examples 1-4

| Time/h | HA release rate/% | | | |
|---|---|---|---|---|
| | 1-1 | 1-2 | 1-3 | 1-4 |
| 2 | 3.2 | 3.1 | 3.6 | 4.2 |
| 4 | 9.3 | 11.2 | 15.9 | 18.3 |
| 8 | 20.7 | 25.3 | 29.7 | 32.8 |
| 12 | 33.4 | 40.6 | 45.7 | 47.2 |
| 20 | 47.9 | 52.1 | 55.3 | 56.7 |
| 30 | 59.3 | 63.8 | 66.5 | 69.5 |
| 45 | 76.8 | 79.3 | 78.6 | 80.5 |
| 60 | 80.6 | 84.9 | 85.7 | 89.2 |

The above results show that the cross-linked hyaluronic acid cell gel material prepared by the method of the present disclosure has excellent properties, especially has excellent pore diameters and mechanical strength. In addition, the obtained cross-linked hyaluronic acid gel material is good in biocompatibility and has good reduction responsiveness. The cross-linked hyaluronic acid cell gel of the present disclosure can thus be used as tissue engineering scaffold materials, and can also be used for loading anticancer drugs to specific sites to carry out smart release of the anticancer drugs.

The above examples are only for explaining the principle of the present disclosure and not for limiting the present disclosure. Many variations and modifications can be made to the present disclosure within the spirit and scope defined by claims of the present disclosure, and all such variations and modifications are included in the protection of the present disclosure.

What is claimed is:

1. A method for preparing a cross-linked hyaluronic acid gel, comprising carrying out a cross-linking reaction in an alkaline aqueous solution of unmodified hyaluronic acid, wherein N,N-bis(acroloyl)cystamine is used as a cross-linking agent in the cross-linking reaction, wherein the alkaline aqueous solution of unmodified hyaluronic acid is prepared by dissolving unmodified hyaluronic acid into a 1% (w/v) alkaline aqueous solution and subsequently the cross-linking agent is added to the alkaline aqueous solution, and wherein a mass ratio of the unmodified hyaluronic acid to the cross-linking agent is 4:1 to 10:1.

2. The method according to claim 1, wherein the cross-linking reaction is carried out for 10 to 18 hours.

3. The method according to claim 1, wherein the cross-linking reaction is carried out at a temperature ranging from 40 to 50° C.

4. The method according to claim 1, wherein after the cross-linking reaction is completed, dialysis and freeze drying are carried out so as to obtain the cross-linked hyaluronic acid gel; wherein a phosphate buffer for the dialysis preferably has a concentration of phosphate ranging from 0.1 to 0.2 M, and a pH value ranging from 7.0 to 7.4.

5. The method according to claim 1, wherein, after the cross-linking reaction is completed, dialysis and freeze drying are carried out so as to obtain the cross-linked hyaluronic acid gel, the dialysis being carried out for 36 to 68 hours.

6. The method according to claim 1, wherein, after the cross-linking reaction is completed, dialysis and freeze drying are carried out so as to obtain the cross-linked hyaluronic acid gel, the freeze drying comprising a first-stage pre-freezing at a temperature ranging from −65 to −45° C. for 2 to 6 hours, a second-stage sublimation being carried out at a temperature ranging from −30 to −25° C. for 4 to 8 hours and then at a temperature ranging from −10 to 0° C. for 3 to 8 hours, and a third-stage desorption drying at a temperature ranging from 5 to 25° C. for 3 to 8 hours.

7. A cross-linked hyaluronic acid gel prepared by the method according to claim 1.

8. A cross-linked hyaluronic acid gel prepared by the method according to claim 2.

9. A cross-linked hyaluronic acid gel prepared by the method according to claim 3.

10. A cross-linked hyaluronic acid gel prepared by the method according to claim 4.

11. A cross-linked hyaluronic acid gel prepared by the method according to claim 5.

12. A cross-linked hyaluronic acid gel prepared by the method according to claim 6.

13. A method for preparing a cross-linked hyaluronic acid gel comprising: (1) dissolving unmodified hyaluronic acid in a 1% (w/v) alkaline aqueous solution; (2) adding N,N-bis (acroloyl)cystamine to the alkaline solution; and (3) carrying out a cross-linking reaction between N,N-bis(acroloyl)cystamine and the unmodified hyaluronic acid at a temperature ranging from 40 to 50° C. for 10 to 18 hours; wherein a mass ratio of the unmodified hyaluronic acid to the N,N-bis (acroloyl)cystamine is 4:1 to 10:1.

14. The method according to claim 13, wherein after step (3), a dialysis is carried out in a 0.1 to 0.2M phosphate buffer at a pH value from 7.0 to 7.4 for 36 to 68 hours.

15. The method according to claim 14, wherein after the dialysis, a freeze drying is carried out, wherein the freeze drying comprises a first-stage pre-freezing at a temperature ranging from −65 to −45° C. for 2 to 6 hours, a second-stage sublimation being carried out at a temperature ranging from −30 to −25° C. for 4 to 8 hours and then at a temperature ranging from −10 to 0° C. for 3 to 8 hours, and a third-stage desorption drying at a temperature ranging from 5 to 25° C. for 3 to 8 hours.

* * * * *